(12) United States Patent  (10) Patent No.: US 9,379,652 B2
Favreau                    (45) Date of Patent:    *Jun. 28, 2016

(54) MOTOR HEALTH MONITORING AND MEDICAL DEVICE INCORPORATING SAME

(71) Applicant: MEDTRONIC MINIMED, INC., Northridge, CA (US)

(72) Inventor: Jacques L. Favreau, Pasadena, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 379 days.

This patent is subject to a terminal disclaimer.

(21) Appl. No.: 13/945,737

(22) Filed: Jul. 18, 2013

(65) Prior Publication Data

US 2013/0303989 A1  Nov. 14, 2013

Related U.S. Application Data

(63) Continuation of application No. 13/425,190, filed on Mar. 20, 2012, now Pat. No. 8,523,803.

(51) Int. Cl.
*A61M 5/142* (2006.01)
*H02P 8/14* (2006.01)
*H02P 29/02* (2016.01)
*A61M 5/145* (2006.01)
*A61M 5/168* (2006.01)

(52) U.S. Cl.
CPC ............... *H02P 8/14* (2013.01); *A61M 5/142* (2013.01); *A61M 5/1452* (2013.01); *A61M 5/14546* (2013.01); *A61M 5/16804* (2013.01); *A61M 5/16831* (2013.01); *H02P 29/022* (2013.01)

(58) Field of Classification Search
CPC ............ A61M 5/172; A61M 5/14244; A61M 5/1452; A61M 2005/16863; A61M 5/142; A61M 2205/33; H02P 8/38; H02P 29/022; H02P 8/14
See application file for complete search history.

(56) References Cited

U.S. PATENT DOCUMENTS

| 3,631,847 | A | 1/1972 | Hobbs, II |
| 4,212,738 | A | 7/1980 | Henne |
| 4,270,532 | A | 6/1981 | Franetzki et al. |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Aarti B Berdichevsky
(74) *Attorney, Agent, or Firm* — Ingrassia Fisher & Lorenz, P.C.

(57) ABSTRACT

Apparatus are provided for motor control systems and related medical devices. In one embodiment, a control system includes a motor having a rotor, a modulation module coupled to the motor, and a control module coupled to the motor and the modulation module. The modulation module generates a modulated voltage that is applied to the motor, and the control module adjusts a duty cycle of the modulated voltage to achieve a commanded rotation of the rotor and detects a degradation condition based on the duty cycle.

20 Claims, 10 Drawing Sheets

(56) References Cited

U.S. PATENT DOCUMENTS

| | | |
|---|---|---|
| 4,282,872 A | 8/1981 | Franetzki et al. |
| 4,334,189 A | 6/1982 | Sato et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,735,887 A | 4/1998 | Barreras, Sr. et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |

(56) References Cited

U.S. PATENT DOCUMENTS

| | | |
|---|---|---|
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,018,361 B2 | 3/2006 | Gillespie, Jr. et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 8,197,444 B1 | 6/2012 | Bazargan et al. |
| 8,202,249 B2 | 6/2012 | Lio et al. |
| 8,362,742 B2 | 1/2013 | Kallmyer |
| 8,469,942 B2 | 6/2013 | Kow et al. |
| 8,523,803 B1 * | 9/2013 | Favreau .............. A61M 5/142 604/67 |
| 8,539,812 B2 | 9/2013 | Stringham et al. |
| 8,603,026 B2 * | 12/2013 | Favreau .............. A61M 5/172 604/67 |
| 8,603,027 B2 * | 12/2013 | Favreau .............. F04B 49/10 604/67 |
| 8,690,855 B2 | 4/2014 | Alderete, Jr. et al. |
| 9,173,993 B2 | 11/2015 | Yodfat et al. |
| 9,216,249 B2 | 12/2015 | Smith et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2011/0092894 A1 | 4/2011 | McGill et al. |
| 2011/0233393 A1 | 9/2011 | Hanson et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO2009/102355 A2 | 8/2009 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

(56) References Cited

OTHER PUBLICATIONS

Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines/MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison/Pump Therapy Will Change Your Life.
(MiniMed, 2000). MiniMed® 508 User's Guide.
(MiniMed Inc., 2000). MiniMed® Now [I] Can Meal Bolus Calculator/MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-dianninobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.

(56) References Cited

OTHER PUBLICATIONS

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artificial Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

MOTOR HEALTH MONITORING AND MEDICAL DEVICE INCORPORATING SAME

CROSS-REFERENCE TO RELATED APPLICATIONS

This application is a continuation of U.S. patent application Ser. No. 13/425,190, filed Mar. 20, 2012. The subject matter described herein is also related to the subject matter described in U.S. patent application Ser. No. 13/425,174 and U.S. patent application Ser. No. 13/425,180, both filed Mar. 20, 2012.

TECHNICAL FIELD

Embodiments of the subject matter described herein relate generally to motor controls and related medical devices, and more particularly, embodiments of the subject matter relate to dynamic control of motors in fluid infusion devices using a modulated voltage.

BACKGROUND

Infusion pump devices and systems are relatively well-known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a stopper (or plunger) in a reservoir. The reservoir cooperates with tubing, a catheter and/or an infusion set to create a fluid path for carrying medication from the reservoir to the body of a user. Some fluid infusion devices also include a force sensor designed to detect and indicate a pump malfunction and/or non-delivery of the medication to the patient due to a fluid path occlusion.

Stepper motors may be used to displace the stopper by a precise amount, and thereby control the dosage administered to a user. Traditionally, a stepper motor is supplied with a direct current (DC) voltage to control and/or maintain position, and thus, the stepper motor continuously consumes power during use. Additionally, stepper motors are frequently controlled using an open-loop control scheme, where the voltage applied to the stepper motor is chosen to be large enough to ensure the stepper motor provides torque that meets or exceeds the likely maximum requirements of the system, thereby ensuring that the stepper motor achieves a number of commanded steps and obviating the need for feedback mechanisms to monitor the position. However, most infusion pump devices and other portable medical devices are battery powered, and accordingly, it is desirable to reduce the power consumption of the stepper motor and prolong battery life.

BRIEF SUMMARY

An embodiment of a motor control system is provided. The system includes a motor having a rotor, a modulation module coupled to the motor, and a control module coupled to the motor and the modulation module. The modulation module generates a modulated voltage that is applied to the motor, and the control module adjusts a duty cycle of the modulated voltage to achieve a commanded rotation of the rotor and detects a degradation condition based on the duty cycle.

Also provided is an embodiment of an infusion device. The infusion device includes a motor having a rotor and a shaft mechanically coupled to the rotor that is displaced to deliver fluid in response to rotation of the rotor. A modulation module is coupled to the motor and generates a modulated voltage that is applied to the motor. A control module is coupled to the modulation module to adjust a duty cycle of the modulated voltage to achieve a commanded rotation of the rotor and identify a degradation condition based on the duty cycle.

In another embodiment, a method for detecting degradation in a drive system is provided. The method involves applying a modulated voltage to a motor, adjusting a duty cycle of the modulated voltage to achieve a commanded rotation of a rotor of the motor, and identifying a degradation condition based on the duty cycle.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
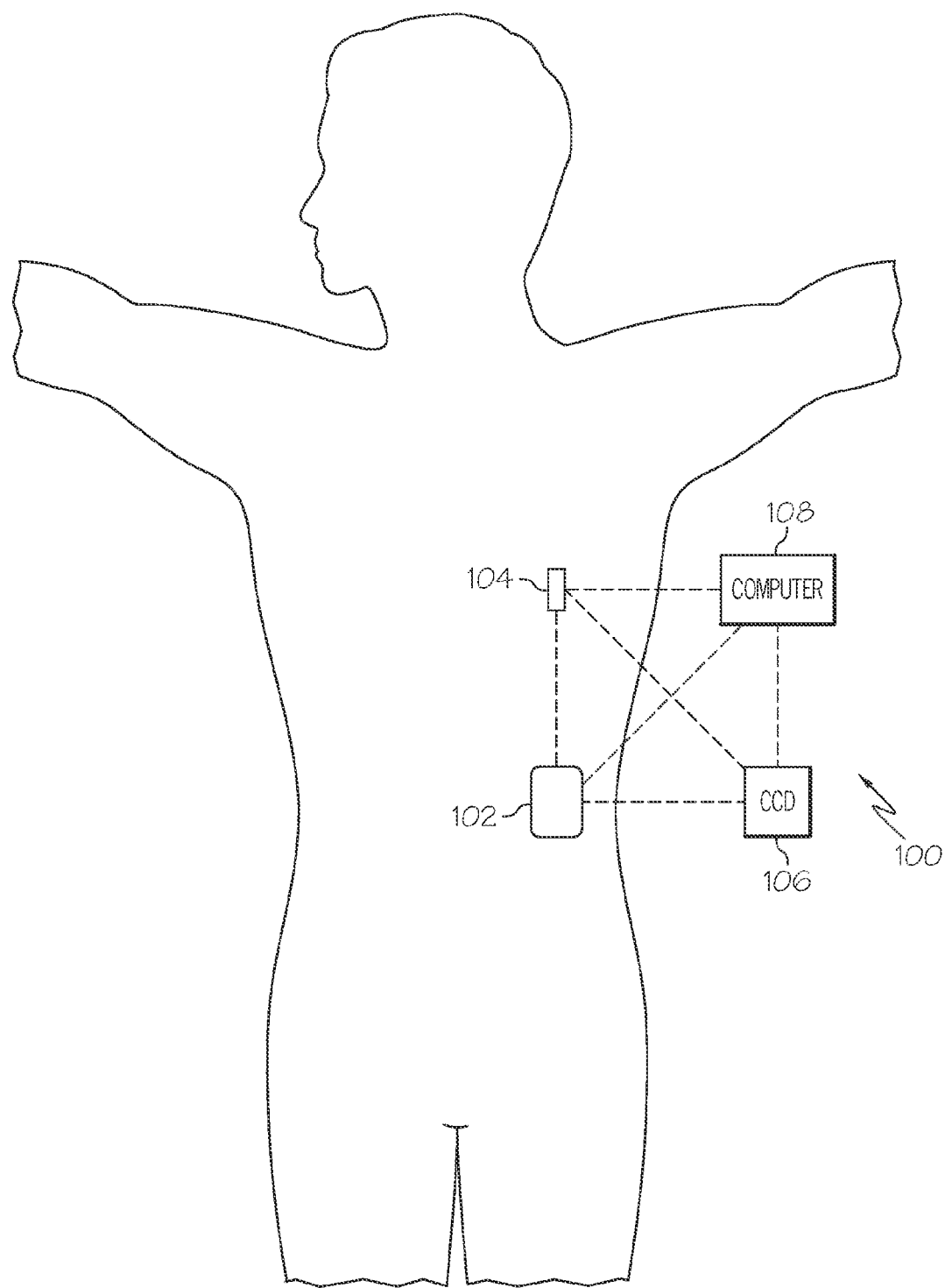
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Embodiments of the subject matter described herein generally relate to controlling the displacement (or rotational position) of a motor by dynamically adjusting the duty cycle of a modulated voltage, such as a pulse-width modulated voltage, that is applied the motor. In exemplary embodiments, a pulse-width modulated voltage is applied to the motor and the motor is operated to produce a commanded amount of rotation (or displacement). Based on the commanded amount of rotation, an expected displacement, either of the rotor or another element mechanically coupled to the rotor, that is expected to result from the commanded amount of rotation is determined and compared to a measured displacement obtained from a sensor after the motor is operated to produce the commanded amount of rotation. In response to a difference between the expected displacement and the measured displacement, the duty cycle of the pulse-width modulated voltage is increased and the motor is operated to compensate for the difference between the expected displacement and the measured displacement while a pulse-width modulated voltage having the increased duty cycle is applied.

In exemplary embodiments, the motor is a stepper motor or another direct current (DC) motor that is commanded to produce a particular number of motor steps, and the sensor is an incremental position sensor (e.g., a rotary encoder) that measures or otherwise detects incremental rotations of the rotor, wherein the expected displacement is the number of incremental rotations of the rotor that are expected to be detected by the incremental position sensor when the stepper motor achieves the commanded number of motor steps and the measured displacement is the actual measured number of incremental rotations identified via the incremental position sensor. However, it should be noted that the subject matter is not limited to stepper motors or incremental position sensors that detect motor rotation. For example, in some embodiments, the sensor may measure or otherwise detect the position or displacement of the shaft of a stopper (or plunger) that is mechanically coupled to the rotor of the motor, wherein the expected displacement is the displacement (or position) of the shaft (or stopper) that should result from the commanded amount of rotation of the rotor and the measured displacement (or position) is the actual measured displacement (or position) of the shaft via the sensor. As described in greater detail below, in exemplary embodiments, the duty cycle of the pulse-width modulated voltage is monitored during operation of the motor to detect an anomalous condition, such as an occlusion condition or a degradation condition, based on the duty cycle. In this regard, when changes in the duty cycle are indicative of an anomalous condition, a notification is generated to alert a user or a supervisory control system of the potential anomaly.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893 which are herein incorporated by reference.

Turning now to FIG. 1, in exemplary embodiments, an infusion system 100 includes, without limitation, a fluid infusion device (or infusion pump) 102, a sensing arrangement 104, a command control device (CCD) 106, and a computer 108. The components of an infusion system may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, assigned to the assignee of the present application, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like. The sensing arrangement 104 generally represents the components of the infusion system 100 configured to sense a condition of the user, and may include a sensor, a monitor, or the like, for providing data indicative of the condition that is sensed and/or monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108. In various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in various embodiments, the CCD 106 and/or the computer 108 include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 may utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, and 7,323,142, all of which are incorporated herein by reference in their entirety. In such embodiments, the sensing arrangement 104 is configured to sense a condition of the user, such as, blood glucose level or the like. The infusion device 102 may be configured to deliver fluid in response to the condition sensed by the sensing arrangement 104. In turn, the sensing arrangement 104 may continue to sense a new condition of the user, allowing the infusion device 102 to deliver fluid continuously in response to the new condition sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
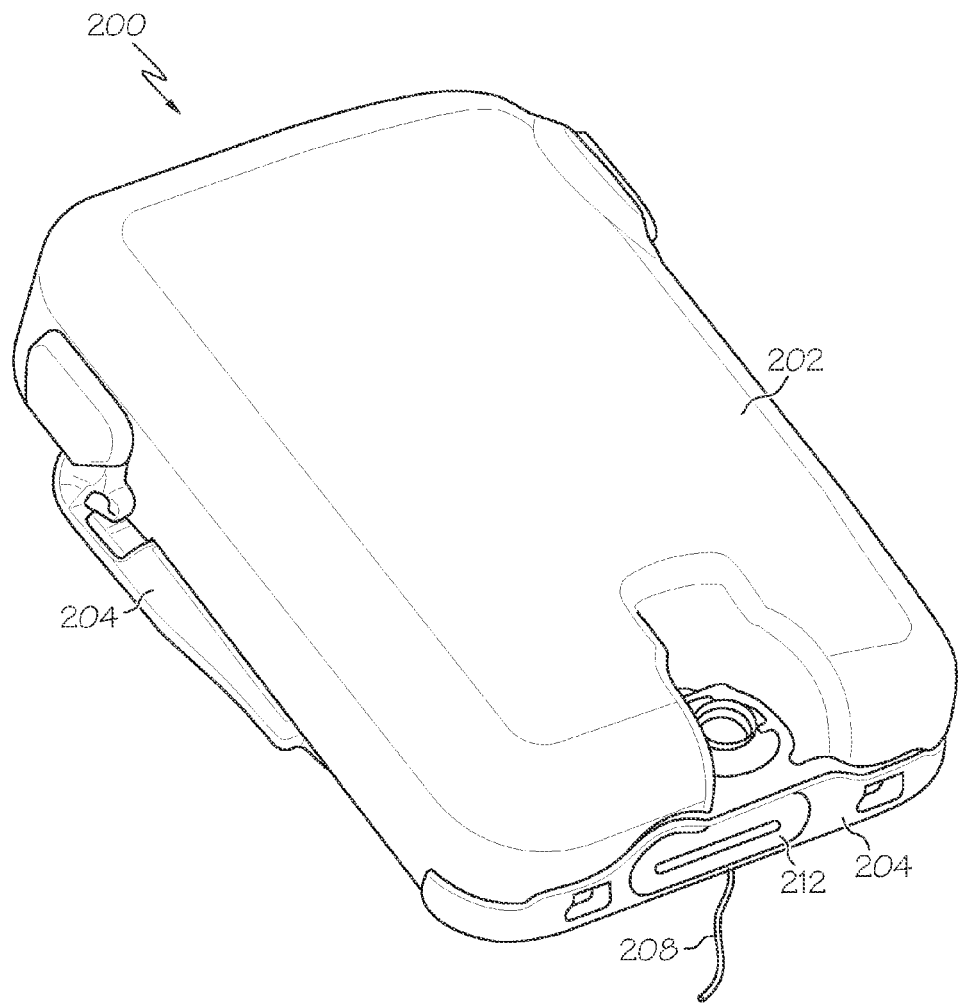
FIG. 2 is a perspective view of an embodiment of a fluid infusion device suitable for use in the infusion system of FIG. 1.
Figure 3:
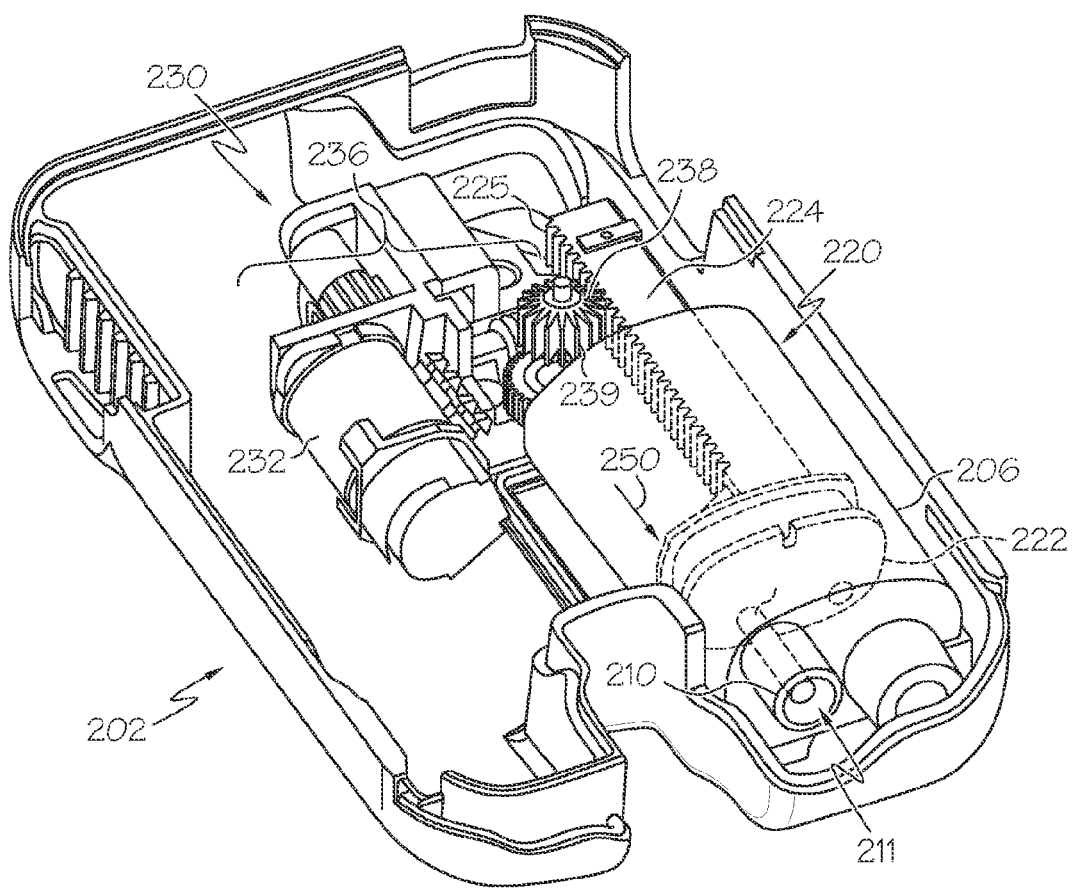
FIG. 3 is a perspective view that depicts internal structure of the durable housing of the fluid infusion device shown in FIG. 2.

Referring now to FIGS. 2-3, in an exemplary embodiment, the infusion device 102 in the infusion system 100 of FIG. 1 is realized as fluid infusion device 200. FIGS. 2-3 depict perspective views of the fluid infusion device 200, which includes a durable housing 202 and a base plate 204. While FIG. 2 depicts the durable housing 202 and the base plate 204 as being coupled together, in practice, the durable housing 202 and/or the base plate 204 may include features, structures, or elements to facilitate removable coupling (e.g., pawls, latches, rails, slots, keyways, buttons, or the like) and accommodate a removable/replaceable fluid reservoir 206. As illustrated in FIG. 3, in exemplary embodiments, the fluid reservoir 206 mates with, and is received by, the durable housing 202. In alternate embodiments, the fluid reservoir 206 mates with, and is received by, the base plate 204.

In exemplary embodiments, the base plate 204 is temporarily adhered to the skin of the user, as illustrated in FIG. 1 using, for example, an adhesive layer of material. After the base plate is affixed to the skin of the user, a suitably configured insertion device or apparatus may be used to insert a fluid delivery needle or cannula 208 into the body of the user. The cannula 208 functions as one part of the fluid delivery path associated with the fluid infusion device 200. The durable housing 202 receives the fluid reservoir 206 and retains the fluid reservoir 206 in a substantially fixed position and orientation while the durable housing 202 and the base plate 204 are coupled. The durable housing 202 is configured to secure to the base plate 204 in a specified orientation to engage the fluid reservoir 206 with a reservoir port receptacle formed in the durable housing 202. In particular embodiments, the fluid infusion device 200 includes certain features to orient, align, and position the durable housing 202 relative to the base plate 204 such that when the two components are coupled together, the fluid reservoir 206 is urged into the reservoir port receptacle to engage a sealing assembly and establish a fluid seal, as described in more detail below.

In exemplary embodiments, the fluid reservoir 206 includes a fluid delivery port 210 that cooperates with the reservoir port receptacle. The fluid delivery port 210 may include a pierceable septum if the fluid reservoir 206 is a prefilled unit. Alternatively, the fluid delivery port 210 may include a vented opening to accommodate filling of the fluid reservoir 206 by the patient, a doctor, a caregiver, or the like. The fluid delivery port 210 has an interior 211 defined therein that is shaped, sized, and otherwise configured to receive a sealing element when the fluid reservoir 206 is engaged with the reservoir port receptacle. The sealing element forms part of a sealing assembly for the fluid infusion device 200. In this regard, the sealing assembly includes one or more sealing elements and/or fluid delivery needles configured to establish fluid communication from the interior of the reservoir 206 to the cannula 208 via the fluid delivery port 210 and a mounting cap 212, and thereby establish a fluid delivery path from the reservoir 206 to the user via the cannula 208.

As illustrated in FIG. 3, the fluid reservoir 206 includes a reservoir barrel 220 that contains the fluid and a stopper 222 (or plunger) positioned to push fluid from inside the barrel 220 of the reservoir 206 along the fluid path through the cannula 208 to the user. The stopper 222 includes a shaft 224 having exposed teeth 225 that are configured to mechanically couple or otherwise engage the shaft 224 of the stopper 222 with a drive system 230 contained in the durable housing 202. In exemplary embodiments, the drive system 230 includes a motor 232 having a rotor that is mechanically coupled to a gear assembly that translates rotation of the rotor of the motor 232 to translational displacement the stopper 222 in the direction 250 of the fluid delivery port 210. In this regard, in exemplary embodiments, the rotor of the motor 232 is mechanically coupled to a rotary shaft, which, in turn, engages a gear assembly 236 that includes a pinion gear 238 having exposed teeth 239 configured to mate with or otherwise engage the teeth 225 of the shaft 224. The rotary shaft translates rotation (or displacement) of the rotor of the motor 232 into a corresponding rotation (or displacement) of the gear assembly 236 such that the exposed teeth 239 of the pinion gear 238 to apply force to the exposed teeth 225 of the shaft 224 of the stopper 222 in the direction 250 of the fluid delivery port 210 to thereby displace the stopper 222 in the direction 250 of the fluid delivery port 210 and dispense, expel, or otherwise deliver fluid from the barrel 220 of the reservoir 206 to the user via the fluid delivery path provided by the cannula 208. In exemplary embodiments, the motor 232 is realized as a DC motor, such as a stepper motor or brushless DC motor capable of precisely controlling the amount of displacement of the stopper 222 during operation of the infusion device 200, as described in greater detail below.

Figure 4:
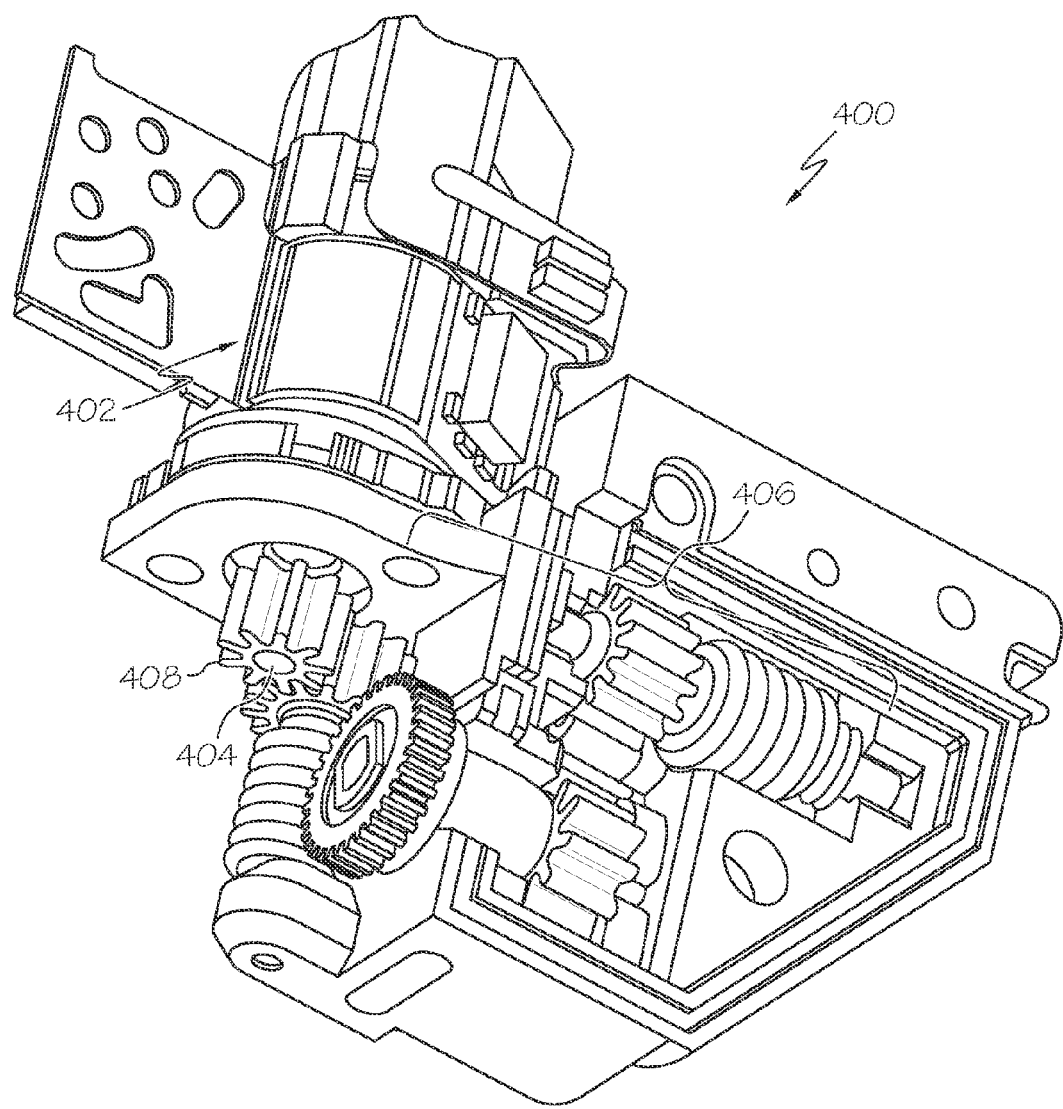
FIG. 4 is a perspective view of an exemplary drive system suitable for use in the durable housing of the fluid infusion device of FIGS. 2-3.
Figure 5:
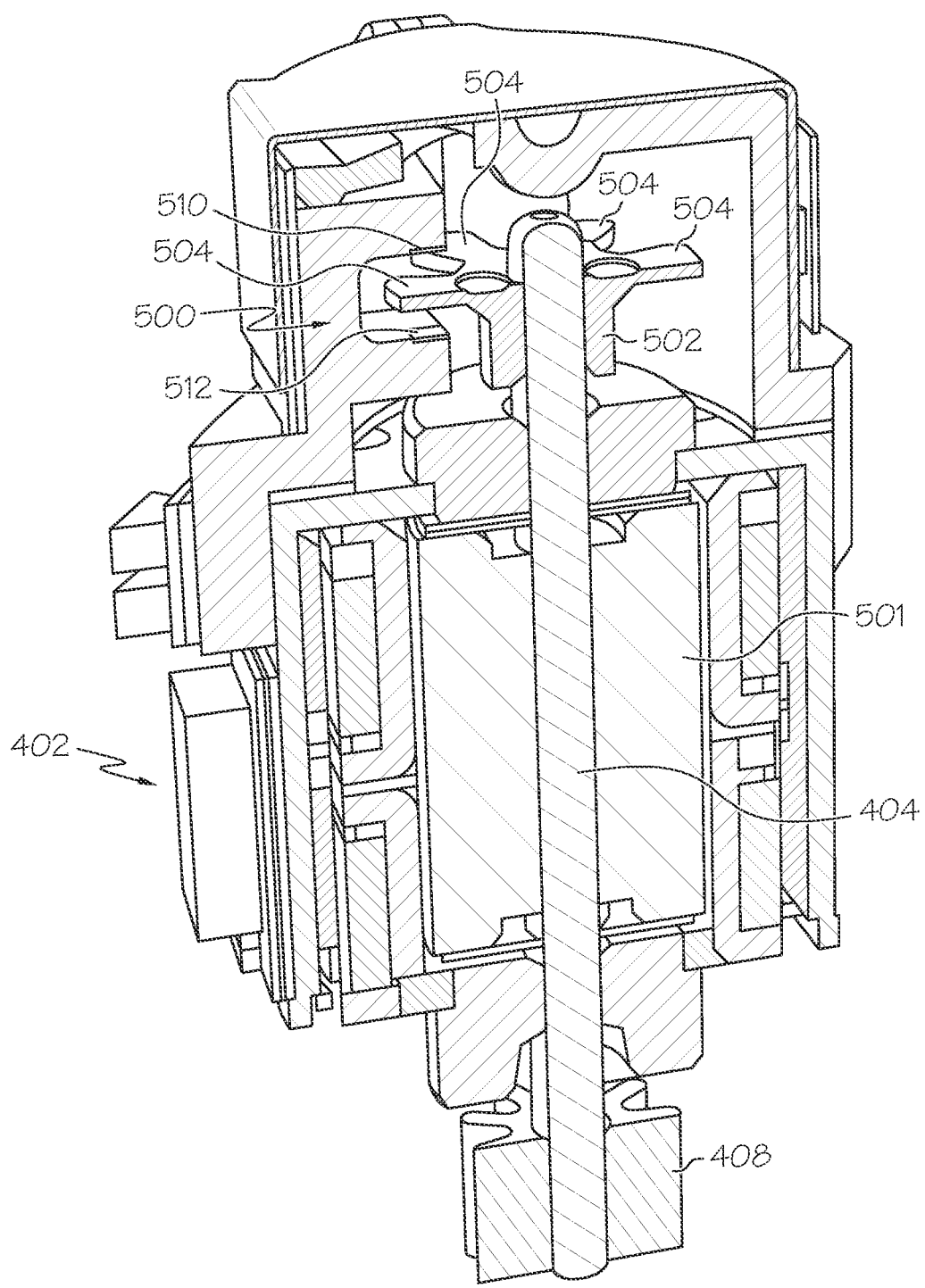
FIG. 5 is cross-sectional perspective view of the motor of motor drive system of FIG. 4 illustrating a sensor integrated therein.
Figure 6:
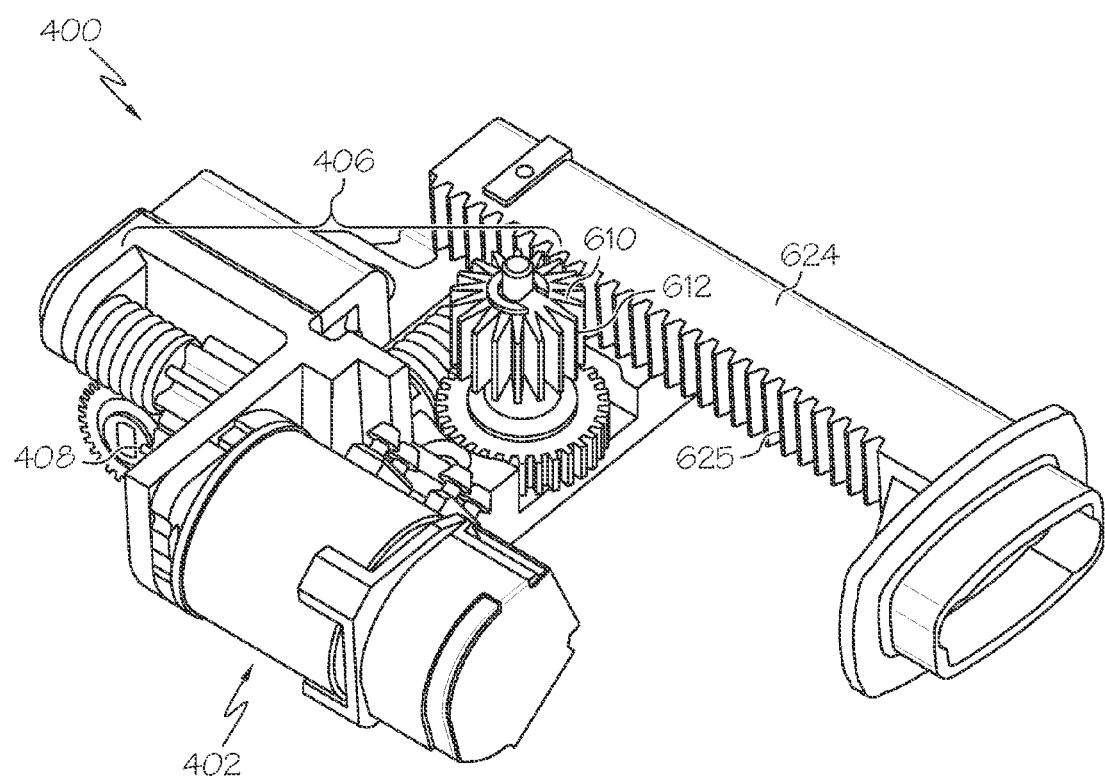
FIG. 6 is a perspective view of the exemplary drive system of FIG. 4 illustrating the gear assembly engaged with a shaft.

Referring now to FIGS. 4-6, in accordance with one or more embodiments, the drive system 230 in the durable housing 202 of the fluid infusion device 200 is realized as drive system 400. In this regard, FIG. 5 depicts a cross-sectional perspective view of the motor 402 of the drive system 400 and FIG. 6 depicts a perspective view of the drive system 400 engaged with a shaft 624, such as the shaft 224 coupled to the stopper 222 of a reservoir 206 in the fluid infusion device 200. Various aspects of the motor drive system 400 may be similar to those described in U.S. patent application Ser. No. 13/049,803. The illustrated drive system 400 includes a motor 402 (e.g., motor 232) and a gear assembly 406 (e.g., gear assembly 236). As described above, the drive system 400 includes a rotary shaft 404 that is mechanically coupled to the rotor 501 of the motor 402. The rotary shaft 404 is mechanically coupled to a first gear 408 of the gear assembly 406. In the illustrated embodiment, the first gear 408 is coaxial and/or concentric to and disposed about the rotary shaft 404, and the first gear 408 is affixed to or otherwise integrated with the rotary shaft 404 such that the first gear 408 and the rotary shaft 404 rotate in unison. The gear assembly 406 includes a second gear 610 (e.g., pinion gear 238) having teeth 612 that are configured to mate with the exposed teeth 625 on a shaft 624 (e.g., teeth 225 on the shaft 224 of the stopper 222), such that rotation or displacement of the second gear 610 produces a corresponding linear displacement of the shaft 624, as described above. In exemplary embodiments, the gear assembly 406 includes various additional gears and other drive train components (e.g., screws, cams, ratchets, jacks, pulleys, pawls, clamps, nuts, slides, bearings, levers, beams, stoppers, plungers, sliders, brackets, guides, bearings, supports, bellows, caps, diaphragms, bags, heaters, and the like) configured to mechanically couple the gears 408, 610 so that rotation (or displacement) of the first gear 408 produces a corresponding rotation (or displacement) of the second gear 610. Thus, during operation of the fluid infusion device 200, when the motor 402 is operated to rotate the rotor 501 of the motor 402, the rotary shaft 404 rotates in unison with the rotor 501 to cause a corresponding rotation of the first gear 408, which, in turn, actuates the gears of the gear assembly 406 to produce a corresponding rotation or displacement of the second gear 610, which, in turn, displaces the shaft 624 (e.g., shaft 224) in a linear direction (e.g., direction 250).

Referring to FIG. 5, in an exemplary embodiment, a sensor 500 is configured to measure, sense, or otherwise detect rotation (or displacement) of the rotary shaft 404 and/or the rotor 501 of the motor 402. In exemplary embodiments, the rotary shaft 404 includes a detectable feature that is measurable or otherwise detectable by the sensor 500. In the illustrated embodiment, a rotary member (or wheel) 502 is provided on the rotary shaft 404 and includes a plurality of protruding features (or arms) 504 that are measurable or otherwise detectable by the sensor 500. In the illustrated embodiment, the wheel 502 is coaxial and/or concentric to and disposed about the rotary shaft 404, and the wheel 502 is affixed to or otherwise integrated with the rotary shaft 404 such that the wheel 502 and the rotary shaft 404 rotate in unison. In this manner, rotation (or displacement) of the wheel 502 corresponds to the displacement of the rotary shaft 404 and/or the rotor 501 of the motor 402.

In exemplary embodiments, the sensor 500 is realized as an incremental position sensor configured to measure, sense, or otherwise detect incremental rotations of the rotary shaft 404 and/or the rotor 501 of the motor 402. For example, in accordance with one or more embodiments, the sensor 500 is realized as a rotary encoder. In alternative embodiments, the sensor 500 may be realized using any other suitable sensor, such as (but not limited to) a magnetic sensor, optical sensor (or other light detector), tactile sensor, capacitive sensor, inductive sensor, and/or the like. In exemplary embodiments, the incremental position sensor 500 may be configured to count or otherwise sense incremental rotations of the motor 402 via the wheel 502, for example, by counting each time a protruding feature 504 passes by the sensor 500. In this regard, when the number of protruding features 504 equals or otherwise corresponds to the number of discrete motor steps of the stepper motor 402, the incremental position sensor 500 counts or otherwise senses the number of motor steps traversed by the rotary shaft 404 and/or rotor of the motor 402. In some embodiments, the sensor 500 includes an emitter 510 and a detector 512 disposed on opposite sides of the wheel 502 such that at least a portion of the protruding features 504 passes between the emitter 510 and the detector 512 as the wheel 502 rotates. In this regard, the sensor 500 may detect or otherwise count each instance when a protruding feature 504 interrupts a transmission from the emitter 510 to the detector 512. Alternatively, the sensor 500 may detect or otherwise count each instance a transmission from the emitter 510 to the detector 512 is uninterrupted or otherwise completed (e.g., via gaps between protruding features 504).

Figure 7:
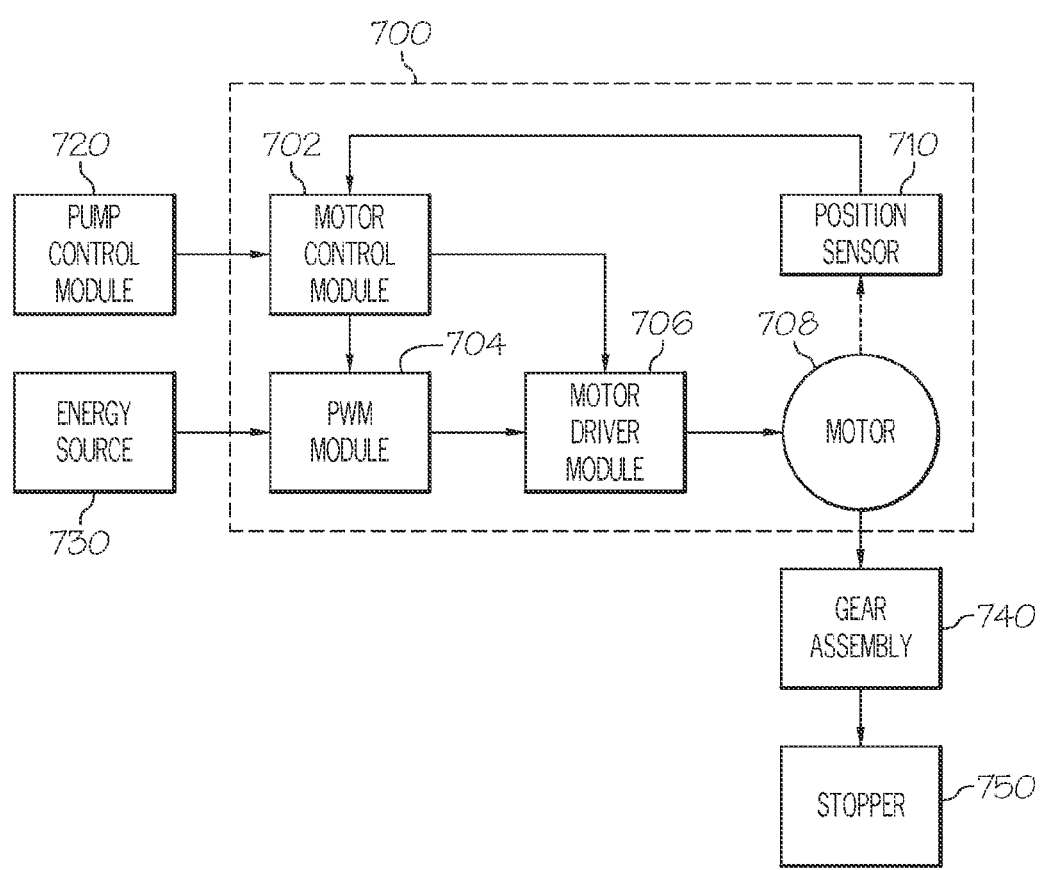
FIG. 7 is a block diagram of an exemplary motor control system suitable for use in the fluid infusion device of FIGS. 2-3.

FIG. 7 depicts an exemplary embodiment of a motor control system 700 suitable for use in a fluid infusion device in an infusion system, such as infusion device 200 or infusion device 102 in the infusion system 100. The illustrated motor control system 700 includes, without limitation, a motor control module 702, a pulse-width modulation (PWM) module 704, a motor driver module 706, a motor 708 (e.g., motor 232, 402), and a position sensor 710 (e.g., sensor 500). In exemplary embodiments, the motor control system 700 is suitably configured to operate the motor 708 to provide a desired amount of fluid to a user in response to a dosage command indicative of the desired amount of fluid to be delivered that is received from a pump control module 720, as described in greater detail below. In this regard, the pump control module 720 generally represents the electronics and other components of the infusion system that process sensor data (e.g., from sensing arrangement 104) pertaining to a condition of the user and control operation of the fluid infusion device according to a desired infusion delivery program in a manner that is influenced by sensor data measured by and/or received from the sensing arrangement 104 or otherwise dictated by the user. In practice, the features and/or functionality of the pump control module 720 may be implemented by control electronics located in the fluid infusion device 102, 200, the CCD 106 and/or the computer 108. It should be understood that FIG. 7 is a simplified representation of the system 700 for purposes of explanation and is not intended to limit the subject matter described herein in any way. For example, in practice, the features and/or functionality of the motor control module 702 may implemented by or otherwise integrated into the pump control module 720, or vice versa.

In the illustrated embodiment, the PWM module 704 generally represents the combination of circuitry, hardware and/or other electrical components configured to generate a pulse-width modulated voltage output applied to the motor 708 via the motor driver module 706. In an exemplary embodiment, the PWM module 704 is coupled to an energy source 730, such as a battery housed within the infusion device 200 (e.g., in the housing 202), to receive a supply voltage. Based on a duty cycle setting for the PWM module 704, the PWM module 704 generates or otherwise produces a pulse-width modulated voltage output that oscillates between the supply voltage provided by the energy source 730 and a ground (or reference) voltage over a time interval (e.g., the PWM period), wherein the pulse-width modulated voltage output is equal to the supply voltage for a percentage of the time interval corresponding to the duty cycle setting. For example, if the supply voltage provided by the energy source 730 is equal to five volts and the duty cycle setting is equal to 30%, then the pulse-width modulated voltage output generated by the PWM module 704 may be a square wave having a magnitude equal to five volts for 30% of the time interval and zero volts for the remaining 70% of the time interval. In this regard, the duty cycle setting corresponds to the width of a portion of the square wave (e.g., the portion corresponding the supply voltage), and accordingly, the duty cycle setting may alternatively be referred to herein as the PWM width setting. In an exemplary embodiment, the frequency of the pulse-width modulated voltage output (e.g., the inverse of the PWM period) is greater than the frequency of the motor driver module 706, as described in greater detail below, and the frequency of the pulse-width modulated voltage output is typically greater than the electrical time constant of the motor coils. As described in greater detail below, in exemplary embodiments, the PWM module 704 is coupled to the motor control module 702 which is configured to adjust, modify, or otherwise control the duty cycle setting of the PWM module 704.

In an exemplary embodiment, the motor 708 is a stepper motor or brushless DC motor having a toothed rotor and a number of sets of windings, wherein the number of teeth on the rotor along with the number of winding sets and the physical arrangement of the winding sets with respect to the rotor teeth provides a finite number of motor steps within a revolution of the rotor. In this regard, as used herein, a "motor step" or any variant thereof should be understood as referring to an incremental rotation of the rotor of the motor 708 that is dictated by the number of teeth of the rotor along with the number and/or arrangement of the winding sets. As described above, in an exemplary infusion pump embodiment, the rotor of the motor 708 is mechanically coupled to a gear assembly 740 (e.g., gear assembly 236, 406) that includes the gears or other drive train components of the infusion device, such that an incremental rotation of the rotor by one motor step produces a corresponding amount of displacement of a stopper 750 (e.g., stopper 222) into a reservoir (e.g., reservoir 206) to deliver fluid (e.g., insulin) to the body of a user.

The motor driver module 706 generally represents the combination of circuitry, hardware and/or other electrical components configured to sequentially apply a voltage provided at a supply voltage input of the motor driver module 706 to one or more sets of windings of the motor 708 in a particular order to produce a corresponding number of commanded motor steps of rotation by the motor 708. In the illustrated embodiment, the supply voltage input of the motor driver module 706 is coupled to the output of the PWM module 704, such that the motor driver module 706 provides the pulse-width modulated voltage from the PWM module 704 to the one or more sets of windings of the motor 708 in a particular order under control of the motor control module 702. In this regard, in some embodiments, the motor driver module 706 is coupled to the motor control module 702 to receive a commanded number of motor steps from the motor control module 702, wherein in response to the commanded number of motor steps, the motor driver module 706 sequentially applies the pulse-width modulated voltage from the PWM module 704 to the sets of windings of the motor 708 in the appropriate order to produce the commanded number of motor steps. In other embodiments, the motor control module 702 may operate the switches and/or other circuitry of the motor driver module 706 to produce the commanded number of motor steps. The frequency at which the motor driver module 706 is operated (e.g., the frequency at which the pulse-width modulated voltage is changed from being applied to one winding set to another winding set) is less than the frequency of the pulse-width modulated voltage output from the PWM module 704, such that the pulse-width modulated voltage output oscillates between the supply voltage and the ground voltage multiple times over the time period (e.g., the inverse of the motor driver frequency) during which the pulse-width modulated voltage output is applied to a particular set of windings of the motor 708.

In an exemplary embodiment, the position sensor 710 is realized as an incremental position sensor, such as a rotary encoder, that is configured to sense, measure, or otherwise detect an incremental rotation of the rotor of the motor 708, in a similar manner as described above in the context of FIG. 5. In exemplary embodiments, the resolution of the position sensor 710 is greater than or equal to the resolution of the motor 708, that is, the number of discrete incremental rotations measurable by the position sensor 710 over one revolution of the rotor of the motor 708 (e.g., the number of detectable features 504) is greater than or equal to the number of discrete motor steps over one revolution of the rotor of the motor 708. The output of the position sensor 710 is coupled to the motor control module 702 to provide dynamic closed-loop PWM control of the motor 708, as described in greater detail below.

Still referring to FIG. 7, the motor control module 702 generally represents the hardware, software, firmware and/or combination thereof that is configured to receive or otherwise obtain a commanded dosage from the pump control module 720, convert the commanded dosage to a commanded number of motor steps, and command, signal, or otherwise operate the motor driver module 706 to cause the motor 708 to produce the commanded number of motor steps. As described in greater detail below in the context of FIG. 8, in exemplary embodiments, the motor control module 702 determines an expected number of incremental rotations of the motor 708 based on the commanded number of motor steps, obtains the measured number of incremental rotations of the rotor of the motor 708 from the position sensor 710, and based on differences between the measured number and the expected number, modifies or otherwise adjusts the PWM width setting of the PWM module 704 to achieve the commanded number of motor steps. Depending on the embodiment, the motor control module 702 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 702, or in any practical combination thereof. In exemplary embodiments, the motor control module 702 includes or otherwise accesses a memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 702. The computer-executable programming instructions, when read and executed by the motor control module 702, cause the motor control module 702 to perform the tasks, operations, functions, and processes described in greater detail below.

Figure 8:
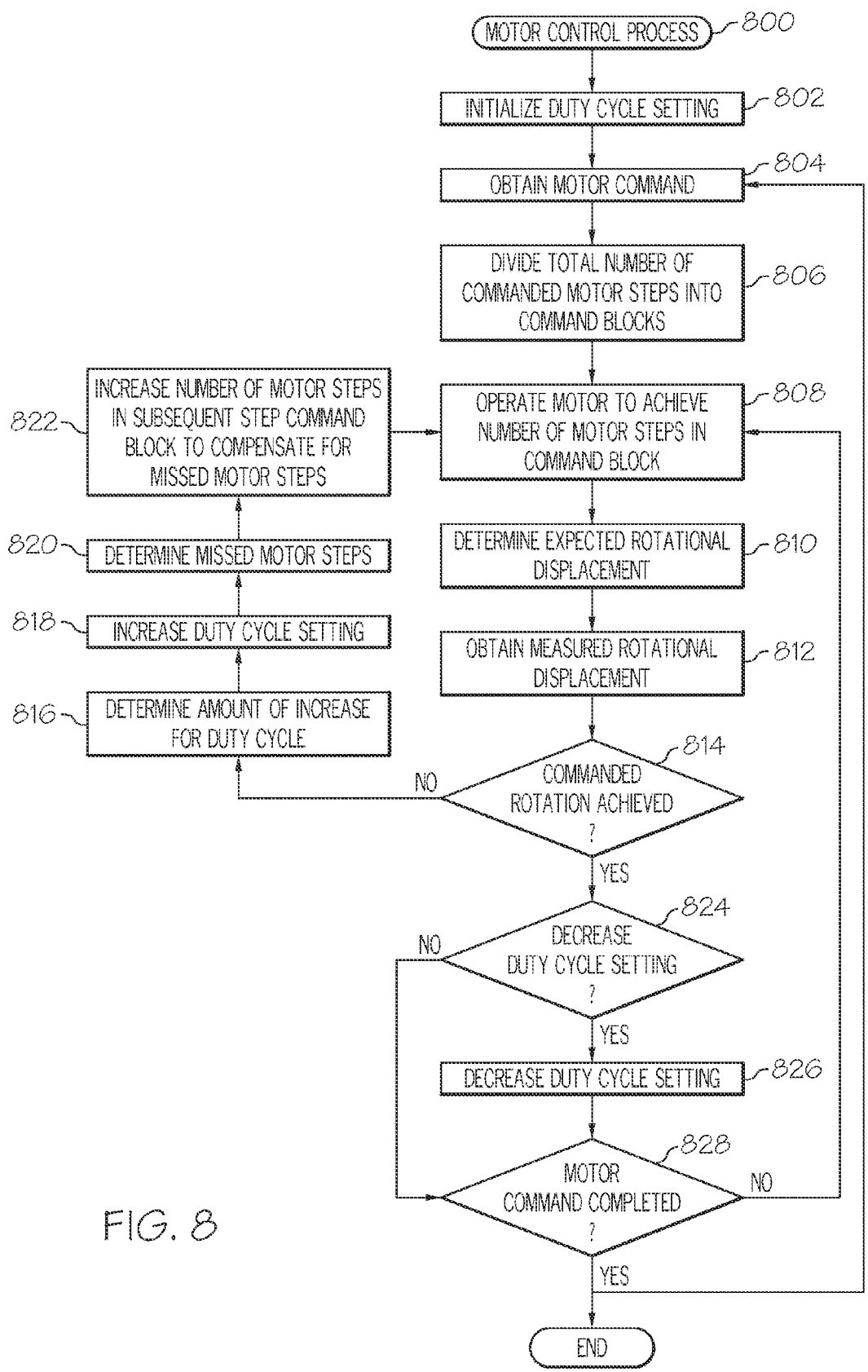
FIG. 8 is a flow diagram of an exemplary motor control process suitable for use with the motor control system of FIG. 7.

FIG. 8 depicts an exemplary motor control process 800 suitable for implementation by a motor control system 700 to deliver fluid to a user using dynamic closed-loop PWM control. The various tasks performed in connection with the motor control process 800 may be performed by software, hardware, firmware, or any combination thereof. For illustrative purposes, the following description refers to elements mentioned above in connection with FIG. 7. In practice, portions of the motor control process 800 may be performed by different elements of the motor control system 700, such as, for example, the motor control module 702, the PWM module 704, the motor driver module 706, the motor 708 and/or the position sensor 710. It should be appreciated that the motor control process 800 may include any number of additional or alternative tasks, the tasks need not be performed in the illustrated order and/or the tasks may be performed concurrently, and/or the motor control process 800 may be incorporated into a more comprehensive procedure or process having additional functionality not described in detail herein. Moreover, one or more of the tasks shown and described in the context of FIG. 8 could be omitted from a practical embodiment of the motor control process 800 as long as the intended overall functionality remains intact.

Referring to FIG. 8, and with continued reference to FIG. 7, the motor control process 800 begins by determining an initial duty cycle setting and configuring the PWM module to implement that initial duty setting (task 802). In an exemplary embodiment, the initial duty cycle setting is a minimum duty cycle capable of rotating the rotor of the motor 708 by one motor step. In this regard, in some embodiments, the motor control module 702 may calibrate or otherwise determine the initial duty cycle setting upon initialization of the infusion pump. For example, upon powering on the infusion pump and/or a reservoir being inserted into the infusion pump, the motor control module 702 may perform a calibration routine by initially setting the duty cycle setting of the PWM module 704 to a minimum value capable of being implemented by the PWM module 704, signaling or otherwise commanding the motor driver module 706 to provide one motor step of rotation, and monitoring the output of the position sensor 710 to determine if the rotor of the motor 708 rotated by a motor step. If the motor 708 did not rotate by a motor step, the motor control module 702 incrementally increases the duty cycle setting of the PWM module 704, repeats the steps of commanding the motor driver module 706 to provide one motor step of rotation and monitoring the output of the position sensor 710 until determining that the rotor of the motor 708 has rotated by a motor step. Once the motor 708 rotates by one motor step, the motor control module 702 maintains the duty cycle setting of the PWM module 704 at the duty cycle that resulted in a motor step of rotation. In other embodiments, the motor control system 700 may be pre-calibrated with an initial PWM width setting that is stored or otherwise maintained by the motor control module 702 for configuring the PWM module 704 upon initialization of the infusion pump and/or the motor control process 800. For example, if the PWM module 704 has a minimum duty cycle setting (e.g., 20%), the motor control module 702 may default the duty cycle setting of the PWM module 704 to the minimum duty cycle capable of being implemented by the PWM module 704.

After configuring the PWM module with an initial duty cycle setting, the motor control process 800 continues by receiving or otherwise obtaining a motor command corresponding to a desired displacement of a stopper or a desired amount of rotation to be provided by the motor (task 804). For example, the pump control module 720 may determine or otherwise receive (e.g., from the CCD 106 and/or the computer 108) a dose (or bolus) of fluid to be provided to the user based on a sensed condition of the user (e.g., a blood glucose level). In some embodiments, the pump control module 720 converts the amount of fluid to be provided to the user into a commanded displacement of the stopper 750, converts the commanded displacement of the stopper 750 to a corresponding number of motor steps, and provides that commanded number of motor steps to the motor control module 702. In other embodiments, the pump control module 720 provides the amount of fluid to be provided to the user to the motor control module 702, wherein the motor control module 702 converts the commanded dosage into a corresponding number of commanded motor steps based on the amount of displacement of the stopper 750 corresponding to that amount of fluid.

In accordance with one or more embodiments, the motor control process 800 continues by dividing or otherwise converting the number of commanded motor steps into a number of step command blocks (task 806). In this regard, in some embodiments, the step command blocks have a fixed number of steps, wherein when the number of commanded motor steps is greater than the fixed number of steps, the motor step command is broken up into smaller command blocks to decrease the response time when the motor 708 fails to achieve a commanded number of motor steps, as described in greater detail below. For example, if the total number of commanded motor steps corresponding to the desired dosage is equal to one hundred motor steps, the motor control module 702 may divide the commanded motor steps into ten different step command blocks of ten motor steps.

In an exemplary embodiment, the motor control process 800 continues by commanding or otherwise signaling the motor driver module to operate the motor in a manner intended to produce the commanded number of motor steps in a step command block with the current PWM width setting (task 808). In this regard, the motor control module 702 signals, commands, instructs, or otherwise operates the motor driver module 706 to sequentially apply the pulse-width modulated voltage output of the PWM module 704 to the various sets of windings of the motor 708 in the appropriate order to cause rotor of the motor 708 rotate by the number of motor steps in the step command block. For example, the motor control module 702 may command the motor driver module 706 to implement ten motor steps, wherein in response, the motor driver module 706 changes which set of windings of the motor 708 that the pulse-width modulated voltage output of the PWM module 704 is applied to ten different times in an order or sequence intended to produce ten motor steps of rotation from the current position of the rotor. As described above, the motor driver module 706 applies the pulse-width modulated voltage output from the PWM module 704 to a first set of windings of the motor 708 for a first time period substantially equal to the inverse of the motor driver module frequency to produce a first motor step of rotation from a current position of the rotor of the motor 708, then applies the pulse-width modulated voltage output from the PWM module 704 to a second set of windings of the motor 708 for another time period substantially equal to the inverse of the motor driver module frequency to produce another motor step of rotation from the updated position of the rotor, and so on until reaching the commanded number of steps in the step command block.

In an exemplary embodiment, the motor control process 800 continues by calculating or otherwise determining an expected displacement of the rotor of the motor or another element mechanically coupled to the rotor (e.g., the stopper) after execution of the step command block based on the commanded number of motor steps in the step command block (task 810). The expected displacement is the amount by which the rotor of the motor 708 is expected to have rotated when the commanded rotation is achieved. To put it another way, the expected displacement corresponds to the amount of displacement of the rotor of the motor 708 that is expected to be measured or detected by the position sensor 710 in response to the commanded rotation. For example, when the position sensor 710 is a rotary encoder or another incremental position sensor, the motor control module 702 calculates or otherwise determines a number of rotational increments that would be expected to be measured or otherwise detected by the position sensor 710 after execution of the step command block based on the number of motor steps in the step command block and the relationship between the resolution of the position sensor 710 with respect to the resolution of the motor 708. In this regard, the expected number of measured rotational increments after execution of a step command block, $n_E$, is equal to $$n_C \times \frac{r_P}{r_M},$$

where $n_C$ is the number of motor steps in the step command block, $r_P$ is the number of discrete rotational increments detectable by the position sensor 710 over a revolution of the rotor of the motor 708, and $r_M$ is the number of discrete motor steps (or discrete rotational increments) for the rotor of the motor 708 over one revolution. Thus, when the number of discrete rotational increments detectable by the position sensor 710 is equal to the number of possible motor steps over a revolution of the motor 708, the expected number of measured rotational increments is equal to the commanded number of motor steps in the step command block.

Still referring to FIG. 8, the motor control process 800 continues by obtaining a measured displacement of the rotor of the motor or another element mechanically coupled to the rotor (e.g., the stopper) after executing the step command block (task 812). In this regard, after commanding the motor driver module 706, the motor control module 702 waits for an amount of time required to implement the step command block before obtaining the position of the rotor of the motor 708 from the position sensor 710. For example, the motor control module 702 may calculate the amount of time required by the motor driver module 706 to implement the step command block by multiplying the number of motor steps in the step command block by the inverse of the motor driver frequency (e.g., the amount of time a pulse-width modulated voltage is applied to produce an individual motor step). When the position sensor 710 is a rotary encoder or another incremental position sensor, the motor control module 702 obtains an initial position of the rotor of the motor 708 from the position sensor 710 (e.g., an initial encoder count) prior to commanding the motor driver module 706 to implement a step command block, obtains a subsequent position of the rotor of the motor 708 from the position sensor 710 (e.g., a subsequent encoder count) after commanding the motor driver module 706 to implement the step command block, and calculates or otherwise determines the measured number of rotational increments as a difference between positions obtained from the position sensor 710 (e.g., by subtracting the initial encoder count from the subsequent encoder count).

In exemplary embodiments, the motor control process 800 identifies or otherwise determines whether the motor has achieved the commanded amount of rotation (task 814). In some embodiments, the motor control module 702 determines that the motor has failed to achieve the commanded amount of rotation when a difference between the expected displacement and the measured displacement exceeds a threshold value. The threshold value is indicative of the number of motor steps of rotation actually achieved by the motor 708 being less than the commanded number of motor steps in the step command block. For example, when the number of discrete rotational increments detectable by the position sensor 710 is equal to the number of possible motor steps over a revolution of the motor 708, the threshold value may be equal to zero. Thus, in such an embodiment, when the expected number of measured rotational increments is greater than the measured number of rotational increments, the motor control module 702 identifies that the motor 708 did not achieve the commanded number of motor steps. In other embodiments where the resolution of the position sensor 710 is greater than the resolution of the stepper motor, the threshold value is chosen to be greater than zero to account for differences between the expected number and the measured number of rotational increments that could be attributable to noise, vibration, or other physical variations and/or misalignment between the position sensor 710 and the rotor teeth and/or positions of the windings sets of the motor 708. For example, if the number of discrete rotational increments detectable by the position sensor 710 over a revolution of the motor 708 is equal to five times the number of motor steps over one revolution, the threshold value may be chosen to be equal to two, such that when the expected number of measured rotational increments is greater than the measured number of rotational increments by more than two, the motor control module 702 identifies that the motor 708 did not achieve the commanded number of motor steps.

In response to identifying that the motor did not achieve the commanded rotation, the motor control process 800 continues by calculating or otherwise determining an amount by which the duty cycle of the PWM module should be increased and increasing or otherwise adjusting the duty cycle setting for the PWM module (tasks 816, 818). In some embodiments, the motor control module 702 calculates an amount by which to increase the PWM width setting based on the difference between the expected displacement and the measured displacement of the motor 708. For example, the motor control module 702 may increase the duty cycle setting of the PWM module 704 by a first amount if the difference between the expected displacement and the measured displacement of the motor 708 corresponds to one missed motor step, increase the duty cycle setting by a greater amount if the difference between the expected displacement and the measured displacement of the motor 708 corresponds to two missed motor steps, and so on. In this regard, the amount of increase to the PWM width setting may correspond to the difference between the expected displacement and the measured displacement of the motor 708. In other embodiments, the motor control module 702 may increase the duty cycle setting by a fixed amount (e.g., a fixed percentage or a percentage of the current duty cycle) regardless of the difference between the expected displacement and the measured displacement of the motor 708. For example, the motor control module 702 may increase the duty cycle setting of the PWM module 704 by 5% each time the motor achieves a number of motor steps that was less than the commanded number of motor steps. After the motor control module 702 identifies or otherwise determines the amount by which to increase the PWM width setting for the PWM module 704, the motor control module 702 determines an updated PWM width setting (e.g., a sum of the previous duty cycle and the amount of increase) for the PWM module 704 and configures the PWM module 704 to implement the updated PWM width setting. For example, if the initial PWM width setting corresponds to a 30% duty cycle and the motor control module 702 determines that the PWM width setting should be increased by 5% based on the difference between the expected number of measured rotational increments and the actual measured number of rotational increments, the motor control module 702 configures or otherwise instructs the PWM module 704 to implement a 35% duty cycle.

In an exemplary embodiment, the motor control process 800 determines the number of missed motor steps based on the measured displacement and modifies the number of motor steps in a subsequent step command block to compensate for the number of missed motor steps (tasks 820, 822). In accordance with one or more embodiments, the motor control module 702 adds a number of motor steps that corresponds to the difference between the expected displacement and the measured displacement to the commanded number of motor steps in the next step command block. In some embodiments, the motor control module 702 may calculate or otherwise determine the actual number of motor steps produced by the motor 708 based on the measured displacement of the rotor and determine the missed motor steps as the difference between the commanded number of motor steps and the actual number of motor steps. For example, when the position sensor 710 is a rotary encoder or another incremental position sensor, the motor control module 702 may convert the measured number of incremental rotations to a number of motor steps and subtract that number of motor steps from the commanded number of motor steps to obtain the missed motor steps. The measured number of incremental rotations may be converted motor steps by multiplying the measured number incremental rotations by $$\frac{r_M}{r_P},$$

where $r_P$ is the number of discrete rotational increments per revolution detectable by the position sensor 710 and $r_M$ is the number of motor steps per revolution. Alternatively, the motor control module 702 may determine the missed motor steps by converting the difference between the expected number of measured incremental rotations and the actual measured number of incremental rotations to a number of motor steps (e.g., by multiplying the difference by $$\frac{r_M}{r_P}).$$

After determining a modified step command block that compensates for missed motor steps, the motor control process 800 continues by commanding or otherwise signaling the motor driver module to operate the motor in a manner intended to produce the number of motor steps in the modified step command block with the updated PWM width setting (task 808). For example, as described above, if the preceding step command block of ten motor steps resulted in two missed motor steps when executed at a PWM width setting of 30%, and the motor control module 702 determines that the PWM width setting should be increased to 35%, the motor control module 702 configures the PWM module 704 to implement a 35% duty cycle while commanding the motor driver module 706 to execute a step command block of twelve motor steps to compensate for the missed motor steps of the previous step command block. While the motor driver module 706 is implementing the modified step command block, the pulse-width modulated voltage oscillates between the supply voltage for 35% of the PWM period and the ground voltage for 65% of the PWM period, rather than oscillating between the supply voltage for 30% of the PWM period and the ground voltage for 70% of the PWM period as was done during the preceding step command block. As described above, the motor control module 702 determines an expected displacement of the rotor of the motor 708 after execution of the modified step command block, obtains a measured displacement of the rotor of the motor 708 after execution of the modified step command block, and determines whether the motor 708 achieved the commanded number of motor steps based on the measured displacement (tasks 810, 812, 814). If the motor 708 did not achieve the number of motor steps commanded during the modified step command block with the updated PWM width setting, the motor control module 702 further increases the PWM width setting for the PWM module and modifies a subsequent step command block to compensate for the missed motor steps during the modified step command block (tasks 816, 818, 820, 822), as described above.

Still referring to FIG. 8, in response to determining that the motor achieved the commanded amount of rotation (e.g., the commanded number of motor steps in a step command block), the motor control process 800 continues by determining whether the duty cycle for the PWM module should be decreased (task 824). In this regard, the duty cycle setting is decreased after the duty cycle has remained unchanged (or constant) and achieved the commanded number of motor steps over a particular amount of time and/or achieved a particular number of commanded motor steps. In some embodiments, the motor control module 702 may store or otherwise maintain a timestamp corresponding to the most recent increase in the PWM width setting and determine that the PWM width setting should be decreased when more than a threshold amount of time has elapsed since the most recent increase in the PWM width setting. For example, the threshold amount of time may be twelve hours, wherein the motor control module 702 obtains a current time and determines the PWM width setting should be decreased when the current time is more than twelve hours after the most recent increase in the duty cycle implemented by the PWM module 704. In other embodiments, the motor control module 702 may count or otherwise monitor a cumulative number of motor steps executed by the motor 708 since the most recent increase in the PWM width setting and determine that the PWM width setting should be decreased when the cumulative number of motor steps executed by the motor 708 since the most recent increase in the duty cycle exceeds a threshold number of motor steps. For example, if the threshold number of motor steps is one thousand motor steps, the motor control module 702 determines the PWM width setting should be decreased when the motor 708 successfully completes one thousand motor steps with a constant duty cycle.

In response to determining the PWM width setting should be decreased, the motor control process 800 continues by decreasing the duty cycle setting for the PWM module (task 826). In some embodiments, the motor control module 702 may decrease the PWM width setting of the PWM module 704 by a fixed amount (e.g., a fixed percentage or a certain percentage of the current duty cycle). In other embodiments, the motor control module 702 may store a previous duty cycle prior to increasing the duty cycle setting, wherein the motor control module 702 decreases the PWM width setting to that previous duty cycle. For example, if the PWM width setting was at a 30% duty cycle prior to increasing to 35%, and the motor 708 has achieved the commanded number of motor steps over a particular amount of time and/or achieved a particular number of commanded motor steps with the 35% duty cycle, the motor control module 702 may revert the PWM width setting of the PWM module 704 back to the 30% duty cycle for subsequent step command blocks.

In an exemplary embodiment, the motor control process 800 continues by determining whether the entire motor command has been completed (task 828). In this regard, the motor control module 702 verifies or otherwise determines whether the rotor of the motor 708 has rotated by the total number of motor steps corresponding to the dose (or bolus) of fluid to be provided to the user. When the motor 708 has not achieved the total number of motor steps corresponding to the desired dosage, the motor control module 702 continues operating the PWM module 704 and the motor driver module 706 until the motor 708 achieves the desired number of motor steps. For example, if not all of the step command blocks corresponding to the motor command have been executed, the motor control module 702 commands or otherwise operates the motor driver module 706 in accordance with the next step command block (task 808), as described above. Once the motor control module 702 determines that the motor 708 has achieved the desired number of motor steps to provide the desired dose of fluid to the user, in an exemplary embodiment, the motor control module 702 turns off the motor driver module 706 until receiving a subsequent motor command.

In response to a subsequent motor command from the pump control module 720 (task 804), the motor control module 702 repeats the steps of operating the motor driver module 706 and dynamically increasing and/or decreasing the PWM width setting of the PWM module 704 based on whether or not the motor 708 achieves a commanded number of motor steps, as described above. The motor 708 consumes power from the energy source 730 only during the times when the pulse-width modulated voltage output of the PWM module 704 is equal to the supply voltage provided by the energy source 730, and thus, by dynamically adjusting the PWM width setting, the power consumed by the motor 708 to achieve a desired number of motor steps may be reduced by keeping the duty cycle setting for the PWM module 704 relatively low and increasing the duty cycle on an as needed basis. As described in greater detail below, in exemplary embodiments, the motor control module 702 monitors the duty cycles provided by the PWM module 704 during operation of the motor control system 700 and detects or otherwise identifies anomalies in the motor control system 700 based on changes to the duty cycle provided by the PWM module 704 that are indicative of an anomalous condition, such as, for example, a degradation condition in the motor 708 and/or the gear assembly 740 or an occlusion condition in a fluid path from the fluid reservoir. In response to identifying an anomalous condition, the motor control module 702 generates a notification that is provided to the pump control module 720 or another supervisory system, which, in turns, notifies the user or initiates remedial action to address the potential anomaly.

Figure 9:
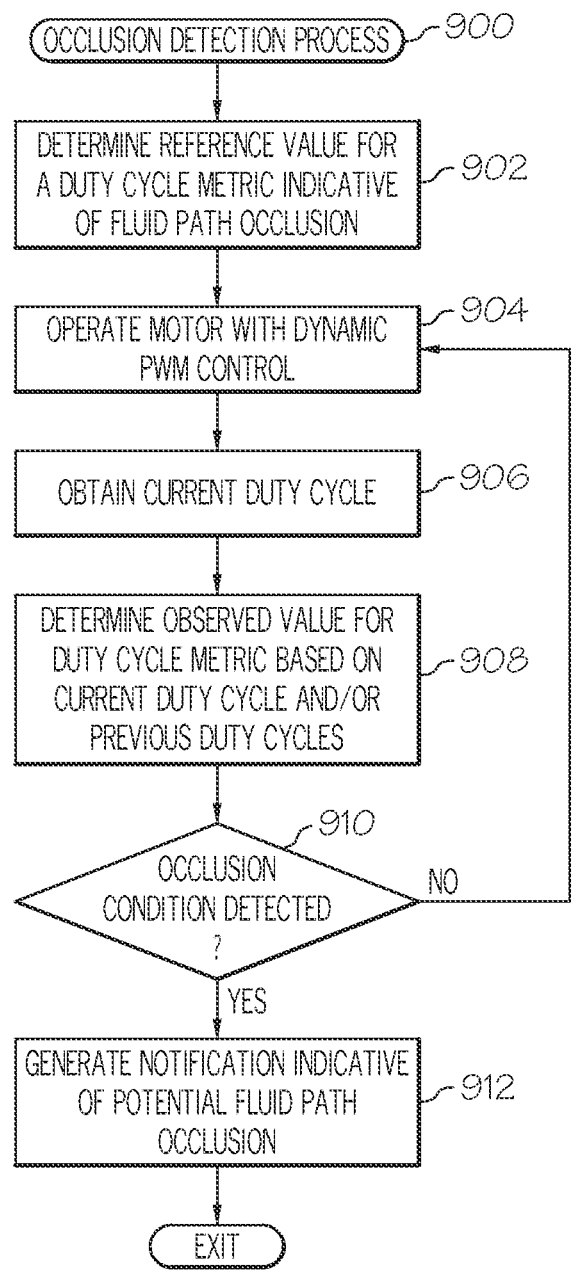
FIG. 9 is a flow diagram of an exemplary occlusion detection process suitable for use with the motor control system of FIG. 7 in connection with the motor control process of FIG. 8.

FIG. 9 depicts an exemplary occlusion detection process 900 suitable for implementation by a motor control system 700 to detect an occlusion in a fluid path while delivering fluid to a user using closed-loop dynamic PWM control in accordance with the motor control process 800 of FIG. 8. The various tasks performed in connection with the occlusion detection process 900 may be performed by software, hardware, firmware, or any combination thereof. For illustrative purposes, the following description refers to elements mentioned above in connection with FIG. 7. In practice, portions of the occlusion detection process 900 may be performed by different elements of the motor control system 700, such as, for example, the motor control module 702. It should be appreciated that the occlusion detection process 900 may include any number of additional or alternative tasks, the tasks need not be performed in the illustrated order and/or the tasks may be performed concurrently, and/or the occlusion detection process 900 may be incorporated into a more comprehensive procedure or process having additional functionality not described in detail herein. Moreover, one or more of the tasks shown and described in the context of FIG. 9 could be omitted from a practical embodiment of the occlusion detection process 900 as long as the intended overall functionality remains intact.

In an exemplary embodiment, the occlusion detection process 900 characterizes the PWM width settings of the PWM module for an occlusion in the fluid path by determining a reference value for a duty cycle metric that is indicative of an occlusion in the fluid path (task 902). In this regard, the reference value for the duty cycle metric is representative of the changes to the duty cycle setting of the PWM module 704 that are likely to be exhibited by the motor control system 700 in response to an occlusion in the fluid delivery path that slows, prevents, or otherwise degrades fluid delivery from the reservoir to a user's body while the motor 708 is operated in accordance with the motor control process 800. In this regard, an occlusion in the fluid path increases the force opposing displacement of the stopper 750, which, in turn, will increase the amount of torque required to rotate the rotor of the motor 708 by a motor step. Depending on the embodiment, the duty cycle metric may be a rate of change (or derivative) of the PWM width setting over a preceding time interval, a moving average of the PWM width setting over a preceding time interval, a sequence of PWM width settings over a preceding time interval, a threshold PWM width value, a matched filter applied to a sequence of PWM width settings over a preceding time interval, or some other metric representative of an occlusion in the fluid path while operating the motor 708 in accordance with the motor control process 800.

In one embodiment, the reference value may be determined by creating or otherwise simulating an occlusion in the fluid path and operating the motor 708 in accordance with the motor control process 800 prior to providing the infusion pump to a user. For example, a component having a known occlusion (e.g., an occluded reservoir, needle, tubing, or the like) may be provided to the infusion pump to create a reference occlusion in the fluid path, and while the reference occlusion exists, the pump control module 720 signals, instructs, or otherwise commands the motor control module 702 to perform a calibration routine by operating the motor 708 for a particular number of motor steps in accordance with the motor control process 800 and monitoring the PWM width settings. In accordance with one embodiment, the number of motor steps used for the calibration routine is greater than the amount of motor steps that are achievable with the reference occlusion in the fluid path. As described above in the context of FIG. 8, the motor control module 702 operates the motor driver module 706 and increases the PWM width settings of the PWM module 704 based on the measured displacement of the motor 708. For example, the motor control module 702 may operate the motor driver module 706 to produce a number of motor steps (e.g., ten motor steps) with the initial PWM width setting, wherein the resistance provided by the reference occlusion prevents the motor 708 and results in an increase in the PWM width setting. As described above, the motor control module 702 may calculate the amount of increase for the PWM width setting based on the difference between the expected displacement and the measured displacement of the motor 708. Thus, when the reference occlusion substantially prevents displacement of the stopper 750 (and thereby prevents rotation of the rotor of the motor 708), the PWM width settings determined by the motor control module 702 may increase at a rate (or by an amount) that is unlikely to occur during normal operation. In exemplary embodiments, the motor control module 702 monitors the PWM width settings determined during execution of the calibration routine and determines the reference value for a duty cycle metric that is indicative of an occlusion based on those PWM width settings (e.g., the amount of change in the PWM width settings during the time interval required to execute the calibration routine, the rate of change or derivative of the PWM width setting during the calibration routine, the sequence of PWM width settings or the sequence of increases to the PWM width settings during the calibration routine, a PWM width settings profile identified for the infusion device using a machine learning algorithm, or the like). After the calibration routine is completed, the reference occlusion is removed before the infusion device is provided to the user.

Still referring to FIG. 9, in an exemplary embodiment, the occlusion detection process 900 continues by operating the motor using dynamic PWM control, obtaining the current PWM width setting for the PWM module, and determining an observed value for the duty cycle metric based on the current PWM width setting and/or previously obtained PWM width settings (tasks 904, 906, 908). In this regard, the motor control module 702 obtains motor commands from the pump control module 720 and operates the motor 708 using dynamic PWM control in accordance with the motor control process 800 of FIG. 8. In an exemplary embodiment, after each step command block executed by the motor driver module 706, the motor control module 702 obtains the current PWM width setting for the PWM module 704 and calculates or otherwise determines an observed value for the duty cycle metric based on the current PWM width setting and/or previously obtained PWM width settings. For example, the motor control module 702 may determine the observed value as an amount of change or rate of change to the PWM width settings over a preceding time interval (e.g., over a preceding time interval equal to the time interval required to execute the calibration routine).

In an exemplary embodiment, the occlusion detection process 900 continues by identifying, detecting, or otherwise determining whether an occlusion condition exists based on the observed value for the duty cycle metric, and in response to detecting an occlusion condition, generating or otherwise providing a notification of the fluid path occlusion (tasks 910, 912). In accordance with one or more embodiments, the motor control module 702 compares the observed value for the duty cycle metric with the reference value indicative of a fluid path occlusion and detects or otherwise identifies an occlusion condition when the observed value meets or exceeds the reference value for the duty cycle metric. For example, if the duty cycle metric is an amount or rate of change to the PWM width setting, the motor control module 702 detects an occlusion condition when the amount or rate of change of the observed PWM width settings is greater than or equal to the amount or rate of change to the PWM width setting during the calibration routine. When the motor control module 702 detects an occlusion condition, the motor control module 702 provides a notification of the fluid path occlusion to the pump control module 720 or another supervisory system or module (e.g., the CCD 106 and/or the computer 108). For example, the motor control module 702 may generate an interrupt signal that is handled by the pump control module 720. In practice, the pump control module 720 and/or the infusion pump may perform other occlusion detection techniques (e.g., using force sensors or the like), wherein the pump control module 720 and/or the infusion pump may utilize the occlusion notification generated by the motor control module 702 to verify, confirm, or otherwise augment the other occlusion detection algorithms and/or techniques performed by the pump control module 720 and/or the infusion pump. In other embodiments, the pump control module 720 and/or the infusion pump may utilize the occlusion notification generated by the motor control module 702 as the sole indicia of a fluid path occlusion when anomalies exist with respect to the other occlusion detection algorithms and/or techniques supported by the infusion device (e.g., damage to other sensors normally relied on for detecting an occlusion). In the absence of a fluid path occlusion, the loop defined by tasks 904, 906, 908 and 910 repeats during operation of the motor 708 in accordance with the motor control process 800 to continuously monitor the PWM width settings of the PWM module 704 for an occlusion condition.

Figure 10:
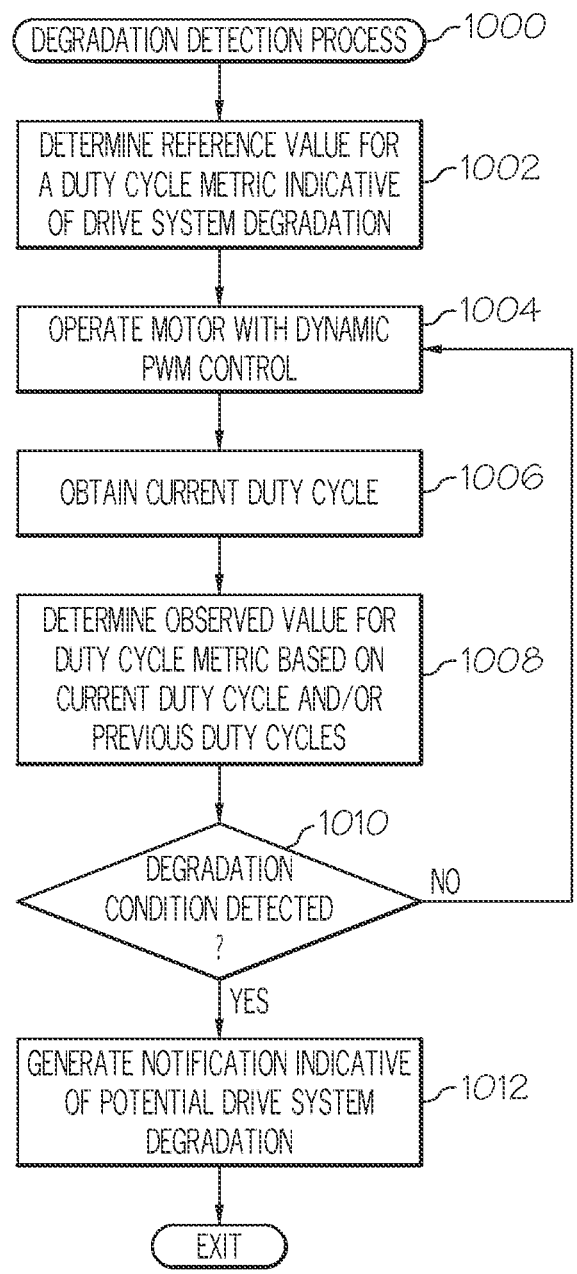
FIG. 10 is a flow diagram of an exemplary degradation detection process suitable for use with the motor control system of FIG. 7 in connection with the motor control process of FIG. 8.

FIG. 10 depicts an exemplary degradation detection process 1000 suitable for implementation by a motor control system 700 to detect wear or degradation in a drive system while delivering fluid to a user using closed-loop dynamic PWM control in accordance with the motor control process 800 of FIG. 8. The various tasks performed in connection with the degradation detection process 1000 may be performed by software, hardware, firmware, or any combination thereof. For illustrative purposes, the following description refers to elements mentioned above in connection with FIG. 7. In practice, portions of the degradation detection process 1000 may be performed by different elements of the motor control system 700, such as, for example, the motor control module 702. It should be appreciated that the degradation detection process 1000 may include any number of additional or alternative tasks, the tasks need not be performed in the illustrated order and/or the tasks may be performed concurrently, and/or the degradation detection process 1000 may be incorporated into a more comprehensive procedure or process having additional functionality not described in detail herein. Moreover, one or more of the tasks shown and described in the context of FIG. 10 could be omitted from a practical embodiment of the degradation detection process 1000 as long as the intended overall functionality remains intact.

In an exemplary embodiment, the degradation detection process 1000 characterizes the drive system by determining a reference value for a duty cycle metric based on the PWM width settings of the PWM module that is indicative of wear or degradation in the drive system (task 1002). The reference value duty cycle metric is representative of the PWM width setting(s) that are likely to be exhibited by the motor control system 700 while the motor 708 is operated in accordance with the motor control process 800 when the motor 708 and/or the gear assembly 740 have experienced sufficient wear or degradation to the point that the motor 708 and/or the gear assembly 740 should be inspected for maintenance, repair and/or replacement. In this regard, reference value is indicates that the motor 708 and/or the gear assembly 740 should be inspected for maintenance, repair and/or replacement. For example, over time, frictional forces in the drive system may accumulate (e.g., due to lubricant wearing out, rust or other surface effects, damage to the motor and/or one or more of the gears, and the like) and increase the force that opposes displacement of the gear assembly 740, the stopper 750 and/or the motor 708, which, in turn, will increase the amount of torque required to rotate the rotor of the motor 708 by a motor step. Thus, the reference value may be a duty cycle that is unlikely to be exceeded (e.g., an 80% duty cycle setting) unless the motor 708 and/or gear assembly 740 has degraded. The duty cycle metric may be a threshold PWM width setting, an average PWM width setting, a sequence of PWM width settings, a matched filter applied to a sequence of PWM width settings over a preceding time interval, or some other metric capable of indicating degradation to the motor 708 and/or the gear assembly 740. For example, the duty cycle metric may be a moving average of the PWM width settings of the PWM module 704 (e.g., an average of the PWM width settings over the previous 24 hours). In this regard, the reference value may be updated or otherwise determined dynamically during operation of the motor control system 700 and/or the infusion device. In some embodiments, the reference value may be the historical duty cycle average over the lifetime of the motor control system 700 and/or the infusion device. For example, the motor control module 702 may continuously obtain the PWM width settings of the PWM module 704 and recalculate the average PWM width setting over the lifetime of the motor control system 700 and/or the infusion pump (e.g., by averaging PWM width settings obtained after each step command block or each motor command), as described in greater detail below.

In an exemplary embodiment, the degradation detection process 1000 continues by operating the motor using dynamic PWM control, obtaining a current duty cycle setting for the PWM module, and determining an observed value for the duty cycle metric based on the current duty cycle setting and/or previously obtained duty cycle settings (tasks 1004, 1006, 1008). As described above, the motor control module 702 obtains motor commands from the pump control module 720 and operates the motor 708 using dynamic PWM control in accordance with the motor control process 800 of FIG. 8. In an exemplary embodiment, after each step command block (or alternatively, after each motor command) executed by the motor driver module 706, the motor control module 702 obtains the current PWM width setting for the PWM module 704 and calculates or otherwise determines an observed value for the duty cycle metric based on the current PWM width setting and/or previously obtained PWM width settings. For example, the motor control module 702 may determine a moving average of the PWM width settings over a preceding time interval (e.g., the previous 24 hours) as the observed value for the duty cycle metric.

In an exemplary embodiment, the degradation detection process 1000 continues by identifying or otherwise determining whether the drive system is exhibiting degradation based on the observed value for the duty cycle metric, and in response to detecting a degradation condition, generating or otherwise providing a notification of the degradation condition (tasks 1010, 1012). The motor control module 702 identifies a degradation condition by comparing the observed value for the duty cycle metric with the reference value indicative of a degradation condition and detecting when the observed value meets or exceeds the reference value. For example, if the reference value is an 80% duty cycle, the motor control module 702 detects a degradation condition when the observed value (e.g., the current PWM width setting of the PWM module 704 or an average of the current and previous PWM width settings) exceeds 80%. Thus, when the duty cycle metric is a moving average of the PWM width settings over a preceding time interval (e.g., the previous 24 hours), the motor control module 702 identifies a degradation condition when the moving average of the PWM width setting exceeds the 80% duty cycle reference value. In some embodiments, the motor control module 702 identifies a degradation condition when the observed value exceeds the reference value by some threshold amount, such as a fixed amount (e.g., a fixed duty cycle percentage) or a fixed percentage of the reference value. In this regard, if the reference value is the average PWM width setting over the lifetime of the motor control system 700 and/or the infusion device, the motor control module 702 may identify a degradation condition when a moving average of the PWM width settings over a shorter time interval exceeds the reference value by more than a threshold percentage of the reference value. For example, if the average PWM width setting over the lifetime of the motor control system 700 corresponds to 50% duty cycle, the motor control module 702 may identify a degradation condition when an average of the PWM width settings over the preceding 24 hours exceeds the reference value by more than fifty percent of the reference value, that is, when the average of the PWM width settings over the preceding 24 hours exceeds a 75% duty cycle. Alternatively, the motor control module 702 may identify a degradation condition when an average of the PWM width settings over the preceding time interval exceeds the reference value by a fixed amount (e.g., a 20% difference in duty cycle).

When the motor control module 702 detects or otherwise identifies a degradation condition, the motor control module 702 provides a notification of the potential degradation to the pump control module 720 or another supervisory system or module. For example, the motor control module 702 may generate an interrupt signal that is handled by the pump control module 720 or another supervisory system, which, in turn, generates an audio and/or visual alert to the user that the drive system should be inspected. In the absence of a degradation condition, the loop defined by tasks 1004, 1006, 1008 and 1010 repeats during operation of the motor 708 in accordance with the motor control process 800 to continuously monitor the PWM width settings of the PWM module 704 for degradation in the drive system.

Referring to FIGS. 7-10, in accordance with one or more embodiments, the motor control process 800, the occlusion detection process 900, and the degradation detection process 1000 are performed by the motor control system 700 concurrently. For example, as described above in the context of FIG. 8, the motor control module 702 may receive motor commands from the pump control module 720 and operate the motor 708 via the PWM module 704 and the motor driver module 706 using closed-loop dynamic PWM control to vary or otherwise adjust the PWM width setting of the PWM module 704 (i.e., the duty cycle of the pulse-width modulated voltage output of the PWM module 704) to achieve the desired rotation of the motor 708, and, in turn, achieve a desired dosage of fluid to the user by displacing the stopper 750 by the desired amount via the gear assembly 740. While operating the motor 708 in accordance with the motor control process 800, the motor control module 702 may obtain the current PWM width settings for the PWM module 704 and determine observed values for the duty cycle metrics used for detecting an occlusion condition or a degradation condition. In this regard, when the PWM width settings for the PWM module 704 rapidly increase or otherwise vary by a certain amount over a relative short period of time in a manner that is characteristic of an occlusion condition, the motor control module 702 detects the occlusion condition and generates a notification of the potential fluid path occlusion, as described above in the context of occlusion detection process 900. In other situations, when the average PWM width settings for the PWM module 704 gradually increase over a longer period of time and exceed a reference value that is characteristic of a degradation condition, the motor control module 702 detects the degradation condition and generates a notification of the potential drive system degradation, as described above in the context of degradation detection process 1000. In this regard, the motor control module 702 may operate the motor 708 using dynamic PWM control to reduce the amount of power consumed by the motor 708 while concurrently monitoring the PWM width settings to identify potential fluid path occlusions or drive system degradation that may impair operation of the infusion pump.

The foregoing description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. In addition, certain terminology may also be used in the herein for the purpose of reference only, and thus is not intended to be limiting. For example, terms such as "first", "second", and other such numerical terms referring to structures do not imply a sequence or order unless clearly indicated by the context.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A system comprising:
   a stepper motor having a rotor and sets of windings;
   a sensor to detect incremental rotations of the rotor;
   a modulation module to generate a modulated voltage oscillating between a first voltage and a second voltage, the modulated voltage being equal to the first voltage for a percentage of a time interval, the percentage corresponding to a duty cycle;
   a motor driver module coupled between the modulation module and the stepper motor to apply the modulated voltage to one or more of the sets of windings; and
   a control module coupled to the sensor, the modulation module, and the motor driver module to:
      operate the motor driver module to sequentially apply the modulated voltage to the one or more of the sets of windings in a particular order to produce a commanded number of motor steps of rotation by the rotor;
      obtain a measured number of the incremental rotations from the sensor after the stepper motor is operated to provide the commanded number of motor steps;
      increase the duty cycle for the modulated voltage in response to a difference between an expected number of incremental rotations corresponding to the commanded number of motor steps and the measured number of the incremental rotations; and
      detect a degradation condition based on the duty cycle.

2. An infusion device, comprising:
   a motor having a rotor;
   a shaft mechanically coupled to the rotor, the shaft being displaced to deliver fluid in response to rotation of the rotor;
   a modulation module coupled to the motor, the modulation module generating a modulated voltage applied to the motor, the modulated voltage oscillating between a first voltage and a second voltage, the modulated voltage being equal to the first voltage for a percentage of a time interval, the percentage corresponding to a duty cycle; and
   a control module coupled to the modulation module to adjust the duty cycle to achieve a commanded rotation of the rotor and identify a degradation condition based on the duty cycle.

3. The infusion device of claim 2, further comprising a sensor to obtain a measured displacement that is influenced by rotation of the rotor, wherein the control module is coupled to the motor and the sensor to operate the motor to provide the commanded rotation of the rotor while the modulated voltage is applied to the motor and adjust the duty cycle for the modulated voltage in response to a difference between an expected displacement corresponding to the commanded rotation the measured displacement obtained after operating the motor to provide the commanded rotation.

4. The infusion device of claim 3, wherein the control module converts a commanded dosage into a commanded displacement of the shaft, the commanded rotation corresponding to the commanded displacement of the shaft.

5. A system comprising:
   a motor having a rotor;
   a modulation module coupled to the motor, the modulation module generating a modulated voltage applied to the motor, the modulated voltage oscillating between a first voltage and a second voltage, the modulated voltage being equal to the first voltage for a percentage of a time interval, the percentage corresponding to a duty cycle; and
   a control module coupled to the motor and the modulation module to adjust the duty cycle to achieve a commanded rotation of the rotor and detect a degradation condition based on the duty cycle.

6. The system of claim 1, wherein the control module detects the degradation condition when the duty cycle gradually increases over a period of time.

7. The system of claim 1, wherein the first voltage comprises a supply voltage and the second voltage comprises a reference voltage.

8. The system of claim 1, the modulated voltage comprising a square wave, wherein the duty cycle corresponds to a width of a portion of the square wave.

9. The system of claim 1, wherein the control module detects the degradation condition when the duty cycle exceeds a reference value.

10. The system of claim 9, wherein the reference value is a duty cycle unlikely to be exceeded unless the motor has degraded.

11. The system of claim 9, wherein the reference value is a historical duty cycle average.

12. The system of claim 9, wherein the control module dynamically determines the reference value during operation of the system.

13. The system of claim 1, further comprising a motor driver module coupled between the modulation module and the motor to apply the modulated voltage to one or more sets of windings of the motor in a particular order to produce a corresponding number of commanded motor steps of rotation by the rotor, wherein the control module is coupled to the motor driver module to operate the motor driver module to provide the commanded rotation of the rotor while the modulated voltage is applied to the one or more sets of windings and increase the duty cycle for the modulated voltage in response to a difference between an expected displacement corresponding to the commanded rotation a measured displacement obtained after operating the motor driver module to provide the commanded rotation.

14. The system of claim 13, wherein a frequency at which the motor driver module is operated to apply the modulated voltage to the one or more sets of windings is less than a frequency of the modulated voltage.

15. The system of claim 14, wherein the frequency of the modulated voltage is greater than a time constant of the motor.

16. The system of claim 1, further comprising a sensor to obtain a measured displacement that is influenced by rotation of the rotor, wherein the control module is coupled to the sensor to increase the duty cycle in response to a difference between an expected displacement and the measured displacement, wherein the expected displacement is based on the commanded rotation of the rotor.

17. The system of claim 16, wherein:
the motor comprises a stepper motor;
the sensor comprises an incremental position sensor to detect incremental rotations of the rotor;
the measured displacement comprises a measured number of the incremental rotations after the motor is operated to provide the commanded rotation; and
the expected displacement comprises an expected number of the incremental rotations expected to be detected by the incremental position sensor after the motor is operated to provide the commanded rotation.

18. The system of claim 16, wherein the control module operates the motor to provide the commanded rotation of the rotor while the modulated voltage is applied to the motor and increases the duty cycle for the modulated voltage in response to the difference between the expected displacement and the measured displacement.

19. The system of claim 18, further comprising a shaft mechanically coupled to the rotor, wherein the commanded rotation corresponds to a commanded displacement of the shaft.

20. The system of claim 18, wherein the control module operates the motor to compensate for the difference between the measured displacement and the expected displacement while the modulated voltage having the increased duty cycle is applied to the motor.

* * * * *